(12) United States Patent
Moore

(10) Patent No.: US 11,878,141 B2
(45) Date of Patent: Jan. 23, 2024

(54) MASKING PACKAGE FOR BLIND TESTING OF MATERIALS STORED IN A SYRINGE

(71) Applicant: Kenneth Simon Aylett Moore, Lymington (GB)

(72) Inventor: Kenneth Simon Aylett Moore, Lymington (GB)

( * ) Notice: Subject to any disclaimer, the term of this patent is extended or adjusted under 35 U.S.C. 154(b) by 208 days.

(21) Appl. No.: 17/277,914

(22) PCT Filed: Sep. 20, 2019

(86) PCT No.: PCT/GB2019/052653
§ 371 (c)(1),
(2) Date: Mar. 19, 2021

(87) PCT Pub. No.: WO2020/058729
PCT Pub. Date: Mar. 26, 2020

(65) Prior Publication Data
US 2022/0118172 A1    Apr. 21, 2022

(30) Foreign Application Priority Data
Sep. 20, 2018 (GB) ...................................... 1815320

(51) Int. Cl.
*A61M 5/00* (2006.01)
*A61M 5/28* (2006.01)

(52) U.S. Cl.
CPC ............ *A61M 5/002* (2013.01); *A61M 5/281* (2013.01); *A61M 2205/32* (2013.01); *A61M 2205/59* (2013.01)

(58) Field of Classification Search
CPC .. A61M 5/002; A61M 5/281; A61M 2205/32; A61M 2205/59
(Continued)

(56) References Cited

U.S. PATENT DOCUMENTS 3,061,129 A    10/1962  Grover
3,642,123 A *   2/1972  Knox ................... B65D 81/133
                                                    604/199
(Continued)

FOREIGN PATENT DOCUMENTS

CH          124023 A     3/1928
EP        2248729 A1    11/2010
(Continued)

OTHER PUBLICATIONS

PCT International Search Report and Written Opinion dated Feb. 25, 2020 for Intl. App. No. PCT/GB2019/052653, from which the instant application is based, 15 pgs.
(Continued)

*Primary Examiner* — Jacob K Ackun
(74) *Attorney, Agent, or Firm* — FREDRIKSON & BYRON, P.A.

(57) ABSTRACT

A masking package (100) for blind testing of materials stored in a syringe, the masking package (100) comprising: an opaque housing (110) defining a syringe chamber (111) adapted to substantially surround a plunger and at least a portion of a barrel of a syringe; and a plunger extender (130) slidably receivable in the syringe chamber (111) and comprising a coupler (132) adapted to couple to the plunger of a syringe received in the syringe chamber (111), wherein movement of the plunger extender (130) relative to the opaque housing (110) moves the plunger of a syringe received in the syringe chamber (111) relative to the barrel of the syringe; and a masking package (200) for blind testing of materials stored in a vial, the masking package (200) comprising an opaque housing (210) defining a chamber (211) for receiving and surrounding a vial, the housing (210) having a length between an upper end and a lower end and comprising a first housing part (212) and a second housing part (214), the first and second housing parts (212, 214)
(Continued)

being openable along the length of the housing (210) to define an opening in the chamber (211) that extends the length of the housing (210) for inserting a vial laterally into the chamber (211), wherein the housing is formed with a single piece construction.

23 Claims, 6 Drawing Sheets

(58) Field of Classification Search
USPC .................................................. 206/364, 365
See application file for complete search history.

(56) References Cited

U.S. PATENT DOCUMENTS

| | | | | |
|---|---|---|---|---|
| 5,031,768 | A * | 7/1991 | Fischer | A61B 50/33 |
| | | | | 206/370 |
| 5,078,267 | A * | 1/1992 | Wright | A61M 5/31525 |
| | | | | 206/364 |
| 5,090,564 | A * | 2/1992 | Chimienti | A61M 5/3205 |
| | | | | 220/4.23 |
| 5,156,267 | A * | 10/1992 | Yates, Jr. | A61M 5/3205 |
| | | | | 220/4.23 |
| 5,293,993 | A * | 3/1994 | Yates, Jr. | A61M 5/3205 |
| | | | | 206/470 |
| 5,370,226 | A * | 12/1994 | Gollobin | A61M 5/3216 |
| | | | | 220/4.23 |
| 5,566,828 | A * | 10/1996 | Claes | B65D 55/14 |
| | | | | 206/570 |
| 5,577,614 | A | 11/1996 | Palmeroni et al. | |
| 5,842,567 | A * | 12/1998 | Rowe | A61B 50/3001 |
| | | | | 206/464 |
| 6,439,276 | B1 * | 8/2002 | Wood | A61M 5/3205 |
| | | | | 141/97 |
| 7,353,946 | B2 * | 4/2008 | Cervantes | A61M 25/002 |
| | | | | 206/428 |
| 2004/0069667 | A1 * | 4/2004 | Tomellini | B65D 85/20 |
| | | | | 206/364 |
| 2006/0037928 | A1 | 2/2006 | Durr | |
| 2012/0006712 | A1 | 1/2012 | Kaplan et al. | |
| 2012/0055929 | A1 | 3/2012 | Hayton et al. | |
| 2012/0296309 | A1 | 11/2012 | Smith et al. | |
| 2013/0149664 | A1 | 6/2013 | San Miguel | |
| 2015/0136639 | A1 | 5/2015 | Aranda Lopez | |
| 2015/0164743 | A1 | 6/2015 | Janson et al. | |
| 2016/0001017 | A1 | 1/2016 | Ogawa | |
| 2022/0133981 | A1 * | 5/2022 | Dumont | A61M 5/31505 |
| | | | | 206/364 |

FOREIGN PATENT DOCUMENTS

| | | |
|---|---|---|
| GB | 2528139 A | 1/2016 |
| WO | 2012080776 A1 | 6/2012 |
| WO | 2016005740 A2 | 1/2016 |

OTHER PUBLICATIONS

Search Report dated Mar. 5, 2019 from corresponding GB Application No. 1815320.5, 4 pgs.
Search Report dated Sep. 3, 2019 from corresponding GB Application No. 1815320.5, 4 pgs.

* cited by examiner

MASKING PACKAGE FOR BLIND TESTING OF MATERIALS STORED IN A SYRINGE

RELATED APPLICATIONS

This application is a 35 U.S.C. 371 national stage filing from International Application No. PCT/GB2019/052653, filed Sep. 20, 2019, which claims priority to British Application No. 1815320.5, filed Sep. 20, 2018, the teachings of which are incorporated herein by reference.

TECHNICAL FIELD

The present invention relates to a masking package adapted to mask medical syringes or vials. In particular, the present invention relates to a masking package for masking medical syringes or vials used in blind clinical trials in order to ensure that participants in the trial remain unaware of which patient is assigned to which treatment group of the study.

BACKGROUND

Clinical trials are clinical studies used to evaluate the effects of new medicaments and new clinical practices. Participants in clinical trials receive a new medicament or a new clinical practice according to a pre-defined therapeutic strategy and the effects of the new medicament or new clinical practice are compared to a currently available treatment or no treatment at all (a placebo). Randomised clinical trials, or randomised controlled trials (RCTs), involve two or more treatment "groups" or "arms", wherein patients in each group receive a different treatment to the patients in the other groups. Blinding is an important procedure in RCTs in which one or more parties involved in the trial is prevented from knowing which patient is assigned to which treatment group of the study. Blinding is intended to remove, as far as possible, conscious or unconscious bias in the design and execution of a trial, which can result in differential treatment of the groups or differential assessment of the outcomes. Depending on the level of blinding, one or more of the patients being treated, the clinical staff administering the treatment, the physician assessing the treatment and the data collectors and analysts interpreting the results may be blinded. In order to minimise the likelihood of differential treatment or assessment of the outcomes, it is generally preferable to blind as many individuals involved with a clinical trial as possible.

RCTs involving liquid medicaments which require delivery to a patient via a hypodermic needle present particular challenges with regard to blinding.

One particular challenge concerns concealing identifying features of the syringes used to administer the medicament. Syringes from different suppliers, containing different medicaments, often have distinctive features which may allow a participant in a study to identify the source of the syringe and the medicament being delivered to a patient via the syringe. Features which may identify the source of a syringe and the medicament within the syringe include, for example: a label on the barrel of the syringe and one or more of the shape, size, material, colour and design of the barrel, a flange of the barrel, the plunger, a flange of the plunger and a rubber stopper of the plunger.

A masked or concealed syringe is required to be functional. In particular, the plunger of a masked syringe must be depressible such that the medicament within the barrel may be delivered to a user. The variations in sizes and shapes between syringes increases the complexity of the challenge of masking syringes. It is particularly desirable to make the height, width and range of motion of all syringes appear identical when masked.

Another particular challenge concerns concealing identifying features of a vial used to store a medicament in an RCT. Vials from different suppliers, containing different medicaments, also often have distinctive features which may allow a participant in a study to identify the source of the vial and the medicament stored within the vial. Features which may identify the source of a vial and the medicament stored within the vial include, for example: a label on the bottle and one or more of the shape, size, material, colour and design of the bottle, a rubber seal at an opening of the bottle and a cap securing the rubber seal in the bottle.

A masked or concealed vial is required to be functional. The medicament stored within the vial will need to be accessible for a clinical practitioner to draw the medicament into a syringe through a hypodermic needle penetrating the rubber seal. The variations in sizes and shapes between vials increases the complexity of the challenge of masking vials. It is particularly desirable to make the procedure for drawing medicament from all vials appear identical when masked.

PRIOR ART

Masking packages for masking medical or hypodermic syringes and vials for syringes are known in the art, as described in international patent application publication number WO 2016/005740 A2, which is an earlier publication from the inventor of the present invention.

In this earlier publication, a masking package for a syringe is described, comprising: an opaque housing; and an adaptor element for fixing a syringe to the housing, wherein the housing is formed of a first housing portion and a second housing portion, the adaptor element is configured to be fixed, in use, to a syringe and an inner surface of the first housing portion, the second housing portion includes an inner surface for engaging with the plunger of a syringe, and wherein the second housing portion can, in use, move relative to the first housing portion to engage and actuate the plunger of a syringe fixed to the adaptor element and first housing portion.

Also in this earlier publication, a masking package for blind testing of materials stored in a container is described, comprising: an opaque housing; and an adaptor element for fixing a container to the housing; wherein the housing is formed of a first housing portion and a second housing portion, the adaptor element is configured to be fixed, in use, to a container and an inner surface of the first housing portion, and wherein the second housing portion can, in use, move relative to the first housing portion.

It would be desirable to provide an improved masking package for a syringe and an improved masking package for a vial.

STATEMENT OF INVENTION

First Aspect—Syringe Mask

According to a first aspect of the invention, there is provided a masking package for blind testing of materials stored in a syringe, the masking package comprising: an opaque housing defining a syringe chamber adapted to substantially surround a plunger and at least a portion of a barrel of a syringe received in the syringe chamber; and a plunger extender slidably receivable in the syringe chamber and comprising a coupler adapted to couple to the plunger of a syringe received in the syringe chamber, wherein movement of the plunger extender relative to the opaque housing moves the plunger of a syringe received in the syringe chamber relative to the barrel of the syringe.

Advantageously, providing an opaque housing that is adapted to substantially surround a plunger and barrel of a syringe enables the masking package to obscure the plunger and at least a portion of the barrel of a syringe. The plunger and barrel of the syringe may comprise features indicative of the source of the syringe to medical practitioners and patients using the syringe. For example, the barrel of the syringe may comprise an identifying label that is covered by the opaque housing and the plunger of the syringe may have a rod or a flange with an identifiable colour or an identifiable shape that is covered by the opaque housing.

Definition of "Syringe"

As used herein, the term "syringe" refers to a reciprocating pump for expelling or drawing fluid through an opening. The term "syringe" is a well-known term in the art. Although the main features of a "syringe" will be well known to a person skilled in the art, a description of the main features is provided herein for completeness.

A syringe comprises: a barrel; and a plunger slidably received in the barrel.

The barrel is typically a cylindrical tube having an opening at a proximal end, an opening at a distal end and an internal chamber for receiving the plunger. The barrel typically comprises: a needle receiving portion at the proximal end; and a flange at the distal end. The needle receiving portion of the barrel may comprise a coupler for coupling the barrel to a needle. The coupler may be any suitable type of coupler, such as a screw thread, and in particular a male or female Luer-Lok connection.

The plunger typically comprises: a stopper or a gasket at a proximal end, a flange at a distal end and a rod or a shaft extending between the gasket and the flange. Typically the gasket of the plunger is received in the internal chamber of the barrel with a friction fit. The friction fit provides a seal between the gasket and an internal surface of the chamber, which enables movement of the plunger within the internal chamber to cause a change of pressure within the chamber. The distal end of the plunger typically extends out of the barrel at the opening at the distal end of the barrel.

The plunger is movable in the barrel between a proximal position, wherein the gasket of the plunger is at a proximal end of the barrel, and a distal position, wherein the gasket of the plunger is at a distal end of the barrel. Movement of the plunger in a proximal direction in the internal chamber of the barrel, towards the proximal end of the barrel, causes fluid to be expelled from the internal chamber of the barrel from the opening at the proximal end. Movement of the plunger in a distal direction in the internal chamber of the barrel, towards the distal end of the barrel, draws fluid into the internal chamber of the barrel through the opening at the proximal end.

The flange at the distal end of the barrel and the flange at the distal end of the piston provide stops against which a user's fingers can push to aid movement of the plunger relative to the barrel in the proximal and distal directions.

As used herein, the terms "proximal", "front" and related terms refer to the ends of the syringe and the masking package that are towards or near a patient's skin in use; and the terms "distal" and "rear" and related terms are used to refer to the ends of the syringe and the masking package that are furthest from the patient's skin in use. Put in another way, the term "proximal" refers to the direction pointing towards the patient during an injection while the term "distal" refers to the opposite direction pointing away from the patient during an injection.

Opaque Housing

The masking package comprises an opaque housing. As used herein, the term "opaque housing" is used to refer to a housing that substantially prevents or inhibits light in the visible range of the electromagnetic spectrum from travelling through the housing, such that articles surrounded by the opaque housing are not visible to a medical practitioner or a patient looking at the masking package.

Preferably, the opaque housing entirely surrounds or encloses the parts of a syringe received in the syringe chamber. The opaque housing may surround or enclose a plunger and at least a portion of a barrel of a syringe received in the syringe chamber.

The opaque housing may be any suitable shape. For example, the opaque housing may be tetrahedral, conical or, preferably, cylindrical. In some preferred embodiments, the opaque housing is elongate.

The opaque housing may be any suitable size to accommodate a plunger and at least a portion of a barrel of a syringe. For example, the opaque housing may have a length of between about 6 cm and about 15 cm, preferably between about 7 cm and about 12 cm and more preferably about 10 cm. For example, the syringe chamber may have a width of between about 1.5 cm and about 5 cm, preferably between about 2 cm and about 4 cm and more preferably about 2.5 cm.

The opaque housing may be formed from any suitable material. Typically, the opaque housing is made from a polymeric or plastics material. However, the opaque housing may be made from any opaque material. Suitable materials include: metals, ceramics or composite materials. Particularly suitable materials include polyether ether ketone (PEEK).

The masking package may be formed by any suitable method. In some preferred embodiments, the masking package is moulded. Preferably, the masking package is injection moulded. A moulded package is required to be formed from a mouldable material, typically a plastics material.

Preferably, the opaque housing is formed with a single piece construction. In some preferred embodiments, the opaque housing is moulded as a single moulded piece. In some particularly preferred embodiments, the opaque housing is moulded by injection moulding as a single injection moulded piece.

The opaque housing may be openable to enable a syringe to be inserted into the syringe chamber and closable to enclose at least the plunger and a portion of the barrel in the syringe chamber, masking the plunger and the portion of the barrel in the syringe chamber.

In some embodiments, the opaque housing has a length between a proximal end and a distal end and comprises a first housing part and a second housing part, the first and second housing parts being openable along the length of the housing to define an opening in the chamber that extends the length of the housing for inserting a syringe laterally into the chamber.

As used herein, the term "laterally" refers to a direction substantially perpendicular to the length of an object. For example, lateral insertion of a syringe into the syringe chamber refers to moving the syringe in a direction substantially perpendicular to the length of the syringe to insert the syringe into the syringe chamber.

In some embodiments, the first and second housing parts may be removably couplable to each other. However, preferably the first and second housing parts are formed together with a single piece construction. In some preferred embodiments, the first and second housing parts may be moulded in a single moulding. In some particularly preferred embodiments, the first and second housing parts may be injection moulded in a single moulding.

In some embodiments comprising first and second housing parts, the first and second housing parts may be rotatably couplable to each other. The first and second housing parts may be rotatable between an open position, in which a syringe is insertable into the syringe chamber, and a closed position, in which at least a portion of a syringe received in the syringe chamber is surrounded by the opaque housing. The first and second housing parts may be rotatable by any suitable means, such as a hinge or a pivot. However, preferably the first and second housing parts are integrally formed and are rotatable about a line of weakness connecting the first and second housing parts. The line of weakness may have a reduced thickness compared to the first and second housing parts, such that the line of weakness is easier to deform or bend than the first and second housing parts, which allows the first and second housing parts to rotate about the line of weakness. In other words, the opaque housing may comprise a plastic hinge, wherein the first and second housing parts are rotatably connected by the plastic hinge. The plastic hinge may be formed by a region of the polymer material having a thickness that is reduced compared to the thickness of the first and second housing parts, such that the first and second housing parts may be rotated, relative to each other, about the plastic hinge.

In embodiments comprising first and second housing parts, at least one of the first and second housing parts may comprise a housing locking element for securing the first and second housing parts together in a closed position. The locking element may be any suitable locking element for retaining the first and second parts in the closed position. In some preferred embodiments, the first and second housing parts each comprise cooperating locking elements. For example, one of the first and second housing parts comprises a housing locking element in the form of a protrusion or hook and the other of the first and second housing parts comprises a locking element in the form of a recess or a notch for receiving the protrusion or hook and securing the first and second housing parts in a closed position. At least one of the first and second housing parts may comprise a plurality of locking elements. In embodiments comprising an elongate opaque housing, at least one of the first and second housing parts may comprise a plurality of locking elements spaced along the length of the opaque housing.

Syringe Chamber

The opaque housing defines a syringe chamber. The syringe chamber is sized and configured to receive at least the plunger and a portion of the barrel of a syringe. Preferably, the opaque housing defines a syringe chamber that is sized and configured to surround or enclose a plunger of a syringe and substantially the length of the barrel of a syringe, when the plunger is in a distal positon relative to the barrel (i.e. when the plunger is extended a maximum distance from the distal end of the barrel).

The syringe chamber may be any suitable shape to accommodate a plunger and at least a portion of a barrel of a syringe. For example, the syringe chamber may be tetrahedral, conical or, preferably, cylindrical.

The syringe chamber may be any suitable size to accommodate a plunger and at least a portion of a barrel of a syringe. For example, the syringe chamber may have a length of between about 6 cm and about 15 cm, preferably between about 7 cm and about 12 cm and more preferably about 10 cm. For example, the syringe chamber may have a width of between about 1.5 cm and about 5 cm, preferably between about 2 cm and about 4 cm and more preferably about 2.5 cm.

The syringe chamber may be sized and shaped to accommodate a plurality of sizes of syringe.

The syringe chamber may be configured or adapted to inhibit or prevent movement of a syringe barrel received in the syringe chamber relative to the opaque housing.

The opaque housing may have a length between the proximal end and the distal end. The syringe chamber may be configured or adapted to inhibit or prevent movement of a syringe barrel received in the syringe chamber relative to the opaque housing in the direction of the length of the housing.

In some embodiments, the opaque housing may comprise at least one projection extending radially inwards from an inner surface of the syringe chamber. The at least one projection may be adapted to engage with a flange at the distal end of a barrel of a syringe received in the syringe chamber to inhibit movement of the barrel in the chamber towards the proximal end of the housing.

In some embodiments, the at least one projection may be a plurality of projections. The plurality of projections may comprise at least a pair of projections. The pair of projections extending radially inwards from an inner surface of the syringe chamber. The pair of projections may be spaced apart along the length of the housing to form a gap for receiving a flange at the distal end of a barrel of a syringe received in the syringe chamber. The pair of projections may inhibit movement of the flange of the barrel in the direction of the length of the housing.

In some preferred embodiments, the pair of projections is one of a plurality of pairs of projections. Each pair of projections may be spaced apart along the length of the housing. Each pair of projections may be arranged at a position along the length of the housing to enable a syringe barrel having a particular length to be received in the syringe chamber.

Plunger Extender

The masking package comprises a plunger extended. Providing the masking package with a plunger extender adapted to couple to a plunger of a syringe received in the syringe chamber of the masking package enables the plunger to be moved relative to the barrel of the syringe while the syringe is received in the masking package, without the plunger being visible to a user. As the plunger extender is slidably receivable in the syringe chamber, the syringe extender may be moved relative to the opaque housing in the same sliding manner as the plunger of the syringe relative to the barrel of the syringe.

As used herein, the term "couple" is used to refer to an attachment, connection. The coupler of the plunger extender is adapted to couple or attach or connect to the plunger of the syringe. Typically, the coupler of the plunger extender is adapted to couple to the distal end of the syringe. Where the syringe comprises a flange at the distal end of the plunger, the coupler of the plunger extender may be adapted to couple or attach or connect to the flange at the distal end of the plunger. Preferably, the plunger extender is removably couplable to a plunger of a syringe received in the syringe chamber.

In some embodiments, the coupler of the plunger extender may be adapted to couple to a flange at the distal end of a plunger of a syringe received in the syringe chamber of the housing.

In some preferred embodiments, the plunger extender comprises a shaft extending between a distal end of the plunger extender and the coupler at the proximal end of the plunger extender.

A distal end of the opaque housing may comprise a distal aperture. The distal aperture may be adapted such that the shaft of the plunger extender extends through the distal aperture when the plunger extender is in the distal position relative to the opaque housing. In particularly preferred embodiments, the shaft of the plunger extender comprises a distal locking element towards the distal end of the shaft. The distal aperture and the distal locking element may be adapted to engage with a snap-fit when the shaft of the plunger extender is in a proximal position relative to the opaque housing. Providing a snap fit may provide an audible and tactile indication to a medical practitioner that the contents of the masked syringe have been fully discharged. A snap fit may also inhibit or prevent the plunger of a masked syringe from being drawn back into a distal position after the contents of the syringe have been fully discharged.

In some particularly preferred embodiments, the plunger extender comprises a flange at the distal end of the shaft. The width of the flange may be greater than the width of the distal aperture of the opaque housing. This may prevent or inhibit the plunger extender from being fully received inside the syringe chamber of the opaque housing.

Carriage/Slider

In some preferred embodiments, the masking package further comprises a carriage. The carriage may be slidable over the barrel of a syringe received in the syringe chamber.

The carriage may be movable with the plunger of a syringe received in the syringe chamber. The carriage comprises a proximal end slidably receivable over the barrel of a syringe received in the syringe chamber. The proximal end of the carriage may be configured or arranged to substantially circumscribe the proximal end of the plunger. In other words, the proximal end of the carriage may substantially surround the circumference of the stopper of the plunger of the syringe. Advantageously, the proximal end of the carriage may mask the proximal end of the plunger such that it is not visible to a medical practitioner or a patient regardless of the relative position of the plunger in the barrel of the syringe.

The carriage may further comprise a distal end adapted to interact with at least one of the plunger extender and the plunger of a syringe when the syringe is received in the syringe chamber of the opaque housing. The distal end of the carriage may be adapted to interact with at least one of the plunger extender and the plunger of the syringe such that the carriage is movable relative to the barrel of the syringe by movement of the plunger extender into a proximal position relative to the opaque housing.

The carriage has a length between the proximal and distal ends. Preferably, the length of the carriage is substantially the same as the length of the plunger of a syringe received in the syringe chamber or is greater than the length of the plunger of the syringe.

The distal end of the carriage may be adapted to interact with at least one of the plunger extender and the plunger of the syringe in any suitable manner. In some embodiments, the distal end of the carriage is couplable to at least one of the plunger extender and the plunger of a syringe when the syringe is received in the syringe chamber. The distal end of the carriage may be removably couplable to at least one of the plunger extender and the plunger of the syringe. In some embodiments, the distal end of the carriage may be adapted to contact or abut at least one of the plunger extender and the plunger of a syringe when the plunger extender is moved from a distal position to a proximal position. In these embodiments, the plunger extender or plunger of the syringe may push against the distal end of the carriage when the plunger extender is moved from a distal position to a proximal position to move the carriage in a proximal direction, without attaching or connecting to the carriage.

In some preferred embodiments, a proximal end of the opaque housing comprises a proximal aperture. The carriage and the proximal aperture may be adapted such that at least a proximal end of the carriage is movable through the proximal aperture on movement of the plunger extender into a proximal position relative to the opaque housing. Accordingly, the plunger extender may be operated in a similar manner to the plunger of the syringe and may cause the plunger of the syringe to move, relative to the barrel of the syringe and the opaque housing, in a similar manner to the plunger extender.

In some embodiments, the proximal end of the carriage comprises a proximal locking element. In these embodiments, the proximal locking element of the carriage and the proximal aperture of the opaque housing may be adapted to engage with a snap-fit when the plunger extender is in the proximal position.

Needle Cover Holder

In some preferred embodiments, the opaque housing is a first opaque housing and the masking package further comprises a second opaque housing. The second opaque housing defines a needle chamber for substantially surrounding a needle cover disposed over a needle coupled to a barrel of a syringe received in the syringe chamber of the first opaque housing. Advantageously, the second opaque housing may mask identifying characteristics of a needle cover.

The second opaque housing may be formed from the same material as the first opaque housing. The second opaque housing may be formed from a different material than the first opaque housing. The suitable materials for forming the first opaque housing are also suitable for forming the second opaque housing.

The second opaque housing may comprise a distal opening at a distal end of the second housing for slidably receiving a needle cover and needle in the needle chamber.

The second opaque housing may be configured to remove a needle cover received in the needle chamber from the needle on which it is disposed when the second opaque housing is moved in a proximal direction relative to the needle.

An inner surface of the needle chamber towards the distal opening may comprise a locking element adapted to engage with a distal end face of a needle cover disposed over a needle to inhibit the needle cover from being removed from the needle chamber through the distal opening. Advantageously, this may enable the second opaque housing to remove the needle cover from the needle by moving the second opaque housing in a proximal direction relative to the needle.

A proximal end of the needle chamber may have a width that is greater than the width of the distal opening. Advantageously, this may improve retention of a needle cover in the needle chamber when the needle cover and the second opaque housing are removed from the needle coupled to the syringe received in the first opaque housing. Preferably, the needle chamber has a length that is greater than the length of a needle cover received in the needle chamber.

In some embodiments, the second opaque housing may have a length between the proximal end and the distal end and comprise a first housing part and a second housing part, the first and second housing parts being separable along the length of the opaque housing to define an opening in the needle chamber that extends the length of the second housing for inserting a needle cover and needle laterally into the syringe chamber. The first and second housing parts of the second opaque housing may be rotatably couplable and rotatable between an open position, in which a needle cover and needle are insertable into the needle chamber, and a closed position, in which a needle cover and needle received in the needle chamber are substantially surrounded by the second housing.

Preferably, the second opaque housing is separate from the opaque housing. However, in some embodiments, the second opaque housing is removably couplable to the distal end of the first opaque housing.

Syringe Mask and Syringe

According to this disclosure, there is also provided a masking package for blind testing of materials stored in a syringe according to the first aspect, and a syringe received in the masking package.

In other words, according to this disclosure, there is also provided a masking package for blind testing of materials stored in a syringe, and a syringe received in the masking package, the masking package comprising: an opaque housing defining a syringe chamber adapted to substantially surround a plunger and at least a portion of a barrel of the syringe received in the syringe chamber; and a plunger extender slidably receivable in the syringe chamber and comprising a coupler adapted to couple to the plunger of the syringe received in the syringe chamber, wherein movement of the plunger extender relative to the opaque housing moves the plunger of the syringe received in the syringe chamber relative to the barrel of the syringe.

The masking package may comprise any features of the masking package described above in relation to the first aspect.

Second Aspect—Vial Mask

According to a second aspect of the present invention, there is provided a masking package for blind testing of materials stored in a vial. The masking package comprises an opaque housing defining a vial chamber for receiving and surrounding a vial. The housing has a length between an upper end and a lower end and comprises a first housing part and a second housing part, the first and second housing parts being openable along the length of the housing to define an opening in the vial chamber that extends the length of the housing for inserting a vial laterally into the chamber. The opaque housing is formed with a single piece construction. Advantageously, such construction of a vial mask enables straightforward insertion of a vial into the masking package and facilitates inexpensive methods of manufacture of the vial mask, such as injection moulding.

Definition of "Vial"

As used herein, the term "vial" refers to a container for holding liquids, in particular liquid medicaments. It will be appreciated that the term "vial" is a well-known term in the art. Although the main features of a vial will be well known to a person skilled in the art, a description of the main features of a vial is provided herein for completeness.

A vial comprises a body and a lid.

The body defines a chamber for holding a liquid. Typically the body is a cylindrical tube having an opening at one end.

The body comprises a neck defining the opening to the chamber. Typically the neck has a width that is narrower than the width of the body. Typically the neck comprises a coupler for coupling to the lid. The coupler may be any suitable type of coupler, such as a male or female screw thread.

As used herein, the term "lid" refers to any covering or closure disposable over the opening of the vial body. Typically, the lid comprises a resealable membrane, also referred to herein as a "septum". Typically the septum is formed from an elastomeric material, such as rubber, and enables needles to be inserted into the chamber and removed from the chamber without exposing the contents of the chamber to ambient air.

The lid is couplable to the body of the vial and adapted to cover the opening to the chamber when coupled to the body. The lid is couplable to the body by any suitable means. Typically the lid is securable to the neck of the body. For example, the lid may be a screw closure. In particular, the neck of the body may be provided with a male screw thread and the lid may be provided with a complimentary female screw thread, or vice versa, for coupling or securing the lid to the neck.

The body of the vial may comprise a base at the opposite end of the body to the opening and the neck. The base may be adapted to support the vial on a horizontal surface, with the opening positioned above the surface and the plane of the opening held substantially horizontal such that liquid held inside the container cannot leak from the chamber under the influence of gravity.

The body of the vial may have an "upper end" and an opposite "lower end". As used herein, the end of the body having the neck and the opening may be referred to as the "upper end" of the body and the end of the body having the base may be referred to as the "lower end" of the body.

Opaque Housing

The masking package comprises an opaque housing. Preferably, the opaque housing entirely surrounds or encloses a vial received in the vial chamber.

The opaque housing may be any suitable shape. For example, the opaque housing may be tetrahedral, conical or, preferably, cylindrical. In some preferred embodiments, the opaque housing is elongate.

The opaque housing may be any suitable size to accommodate a vial.

The opaque housing may be formed from any suitable material. Typically, the opaque housing is made from a polymeric or plastics material. However, the opaque housing may be made from any opaque material. Suitable materials include: metals, ceramics or composite materials. Particularly suitable materials include polyether ether ketone (PEEK).

The masking package may be formed by any suitable method. In some preferred embodiments, the masking package is moulded. Preferably, the masking package is injection moulded. A moulded package is required to be formed from a mouldable material, typically a plastics material.

The opaque housing is formed with a single piece construction. In some preferred embodiments, the opaque housing is moulded as a single moulded piece. In some particularly preferred embodiments, the opaque housing is moulded by injection moulding as a single injection moulded piece.

The opaque housing may be openable to enable a vial to be inserted into the vial chamber and closable to enclose the vial in the vial chamber.

In some embodiments, the opaque housing has a length between a proximal end and a distal end and comprises a first housing part and a second housing part, the first and second housing parts being openable along the length of the housing to define an opening in the chamber that extends the length of the housing for inserting a syringe laterally into the chamber.

It is envisaged that the first and second housing parts may be removably couplable to each other. However, preferably the first and second housing parts are formed together with a single piece construction. In some preferred embodiments, the first and second housing parts may be moulded in a single moulding. In some particularly preferred embodiments, the first and second housing parts may be injection moulded in a single moulding.

In some embodiments, the first and second housing parts may be rotatably couplable to each other. The first and second housing parts may be rotatable between an open position, in which a vial is insertable into the vial chamber, and a closed position, in which a vial received in the vial chamber is surrounded by the opaque housing. The first and second housing parts may be rotatable by any suitable means, such as a hinge or a pivot. However, preferably the first and second housing parts are integrally formed and are rotatable about a line of weakness connecting the first and second housing parts. The line of weakness may have a reduced thickness compared to the first and second housing parts, such that the line of weakness is easier to deform or bend than the first and second housing parts, which allows the first and second housing parts to rotate about the line of weakness. In other words, the opaque housing may comprise a plastic hinge, wherein the first and second housing parts are rotatably connected by the plastic hinge. The plastic hinge may be formed by a region of the polymer material having a thickness that is reduced compared to the thickness of the first and second housing parts, such that the first and second housing parts may be rotated, relative to each other, about the plastic hinge.

The first and second housing parts are openable along the length of the housing. Preferably, the first and second housing parts are rotatably moveable or couplable or coupled together. In some embodiments, the second housing part is rotatable relative the first housing part about an axis parallel to the length of the housing. In these embodiments, the first and second housing parts may be rotatably coupled together along the length of the first housing part and the second housing part. In some preferred embodiments, the second housing part is rotatable relative to the first housing part about an axis transverse to the length of the housing. In these preferred embodiments, the first and second housing parts may be rotatably coupled at the lower end of the housing.

In some particularly preferred embodiments, a base portion may be disposed between the first housing part and the second housing part. The lower end of the first housing part may be rotatably coupled to the base portion. The lower end of the second housing part may be rotatably coupled to the base portion. The first housing part and the second housing part may be rotatably coupled together at the lower end by the base portion. In these embodiments, the first and second housing parts are indirectly rotatably coupled together, as each of the first and second housing parts is rotatably coupled to the base portion.

In some particularly preferred embodiments:

the first housing part comprises opposing upper and lower edges and opposing side edges extending between the upper and lower edges;

the second housing part comprises opposing upper and lower edges and opposing side edges extending between the upper and lower edges; and a base portion extends between the lower edges of the first and second housing parts and is rotatably coupled to the lower edges of the first and second housing parts.

In some preferred embodiments, an opening is defined in the housing of the masking package at the upper end of the housing. In some of the particularly preferred embodiments, an opening is defined between the upper edges of the first and second housing parts when the first and second housing parts are together in a closed position. The lid of a vial received in the vial chamber may be located at or around the opening. The opening may be suitable for receiving a needle in the vial chamber to penetrate the lid of a vial received in the vial chamber to draw liquid from the vial. In these embodiments, the housing may further comprise a lid portion rotatably coupled to the upper edge of the second housing part. The lid portion may be rotatable relative to the second housing part between an open position, in which the opening between the upper edges of the first and second housing parts is uncovered, and a closed position, in which the first and second housing parts is covered by the lid portion.

In some embodiments, the opaque housing comprises a window, wherein a portion of a vial received in the vial chamber is visible through the window. The window may be arranged at or around the neck of a vial received in the vial chamber. The window may be arranged at or around a portion of the body of a vial received in the vial chamber. Providing at least one window may enable a user to see how much liquid medicament is held in a vial received in the vial chamber. Preferably, where a window is provided in the opaque housing, the window is arranged so that a label of a vial received within the masking package is not visible through the window.

Vial Support

In some embodiments, at least one of the first and second housing parts comprises a neck support for supporting a neck of a vial received in the vial chamber and inhibiting movement of the vial in the chamber in a direction along the length of the housing. The vial support may comprise at least one protrusion extending radially inwards into the vial chamber towards the upper end of the opaque housing.

In some embodiments, at least one of the first and second housing parts may comprise a plurality of neck supports, spaced apart along in a direction along the length of the housing, for accommodating vials of different sizes within the vial mask. Where the vial mask is configured to receive vials of different sizes, the vial mask is configured to ensure that vials received in the vial chamber are supported in the vial chamber with their lids at the same position in the vial chamber relative to the upper end of the chamber, such that a user inserting a needle into the masked vial cannot determine the vial size based on the position of the lid of the vial in the vial chamber.

In some embodiments, the neck support is removably couplable to the opaque housing.

Providing a neck support within the masking package may ensure that the lid of a vial received in the masking package is positioned correctly at the upper end of the housing. Where an opening is provided in the upper end of the masking package to enable a needle to be inserted into a vial received in the masking package via the lid of the vial, a neck support may ensure that the lid of the vial is arranged adjacent or close to the opening.

Base Support

In some embodiments, at least one of the first and second housing parts comprises a base support for supporting a base of a vial received in the vial chamber The base support may comprise at least one protrusion extending radially inwards into the vial chamber towards a lower end of the opaque housing.

Locking Element

At least one of the first and second housing parts may comprise a locking element for securing the first and second parts together in a closed position.

Any feature in one aspect of the invention may be applied to other aspects of the invention, in any appropriate combination. Furthermore, any, some and/or all features in one aspect can be applied to any, some and/or all features in any other aspect, in any appropriate combination.

Vial Mask and Vial

According to this disclosure, there is also provided a masking package for blind testing of materials stored in a vial according to the second aspect, and a vial received in the masking package.

In other words, according to this disclosure, there is also provided a masking package for blind testing of materials stored in a vial, and a vial received in the masking package, the masking package comprising an opaque housing defining a vial chamber for receiving and surrounding the vial, the housing having a length between an upper end and a lower end and comprising a first housing part and a second housing part, the first and second housing parts being openable along the length of the housing to define an opening in the vial chamber that extends the length of the housing for inserting a vial laterally into the chamber. The opaque housing is formed with a single piece construction.

The masking package may comprise any features of the masking package described above in relation to the second aspect.

The vial comprises a body and a lid. Both the body and the lid of the vial are received in the vial chamber. As such, both the body and the lid of the vial are substantially obscured from view of a user by the masking package.

The body of the vial also comprises a neck at an upper end of the body. Where the masking package comprises a neck support for supporting the neck of the vial in the vial chamber, the neck of the body is received in the neck support. The neck support may be configured with a recess that is configured to receive the neck of the vial. The recess may have a width that is equal to or larger than the neck, by smaller than the width of the lid and lower part of the body of the vial. Such a configuration results in the lid of the vial and the lower part of the body of the vial abutting the neck support when the vial moves within the masking package in the direction of the length of the masking package. As a result, the neck support prevents or inhibits the vial from moving in the direction of the length of the masking package. In some embodiments, the masking package comprises an opening at an upper end to permit access to the lid of the vial received in the vial chamber by a needle and syringe. Advantageously, in these embodiments, the neck support may ensure that the lid of the vial received in the vial chamber is suitably positioned adjacent to the opening at the upper end of the masking package, to enable a needle to access the lid of the vial through the opening.

It should also be appreciated that particular combinations of the various features described and defined in any aspects of the invention can be implemented and/or supplied and/or used independently.

BRIEF DESCRIPTION OF THE DRAWINGS

One or more embodiments of the present invention will now be described by way of non-limiting example only and with reference to the accompanying drawings, in which:

FIGS. 1-6 show a masking package 100 according to an embodiment of the present invention for masking a syringe 10.

FIGS. 1 and 2 show a syringe 10 masked by the masking package 100.

Figure 1:
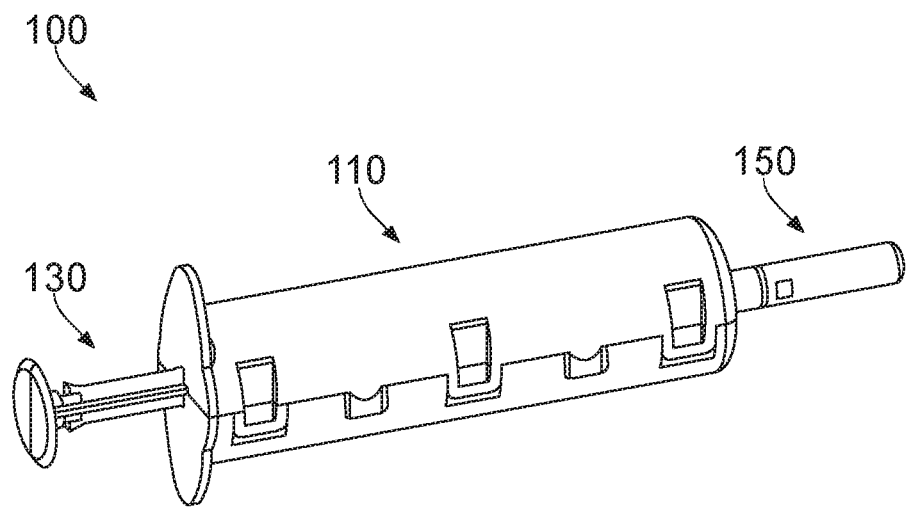
FIG. 1 is a perspective view of a syringe masked by a syringe masking package according to an embodiment of the present invention

The syringe 10 comprises an elongate barrel 12, having an internal chamber for holding liquid medicaments; an open proximal end; and an open distal end. A hypodermic needle (not shown) is attached to the proximal end of the barrel 12. A flange 14 is provided at the distal end of the barrel 12 to provide purchase for a user's fingers. The syringe 10 further comprises a plunger 16 which is slidably received in the internal chamber of the barrel 12 and extends through an aperture at the distal end of the barrel 12. The plunger 16 comprises a stopper 18 at a proximal end, which is received in the chamber of the barrel with an interference fit, a shaft 20 extending from the stopper 18 in a proximal direction and a flange 22 at a distal end, which also provides purchase for a user's fingers during use. Sliding the plunger 16 in a proximal direction, towards the proximal end of the barrel, pushes fluid within the chamber out of the hypodermic needle (not shown) at the proximal end, and sliding the plunger in a distal direction, towards the distal end of the barrel, draws fluid into the chamber through the hypodermic needle at the proximal end. A needle cover (not shown) is provided over the hypodermic needle to maintain sterility of the needle.

Figure 3:
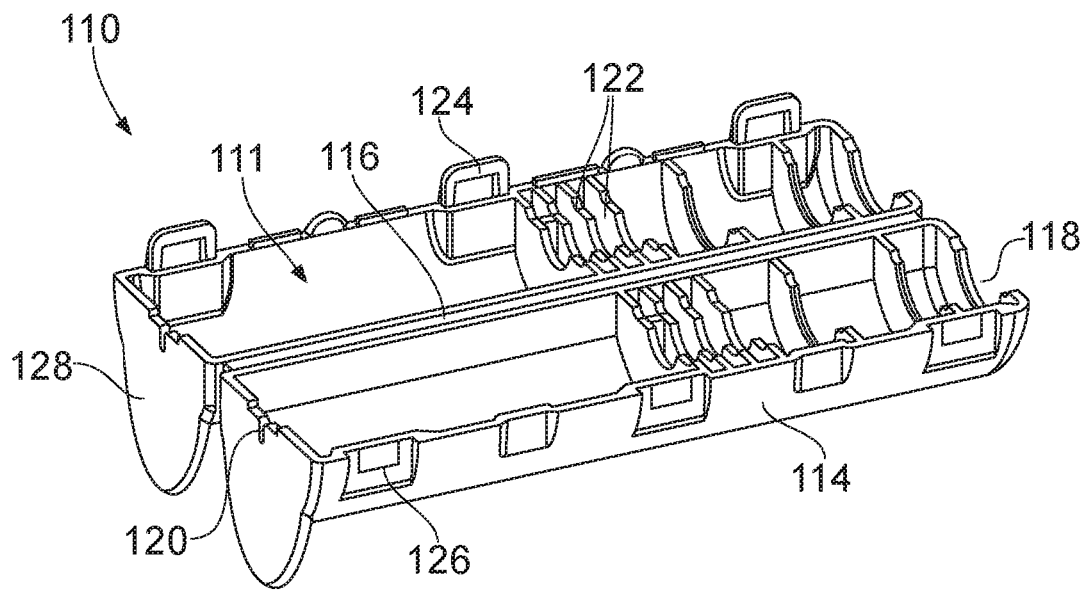
FIG. 3 is a perspective view of the opaque housing of the masking package of FIG. 1, in an open configuration.
Figure 4:
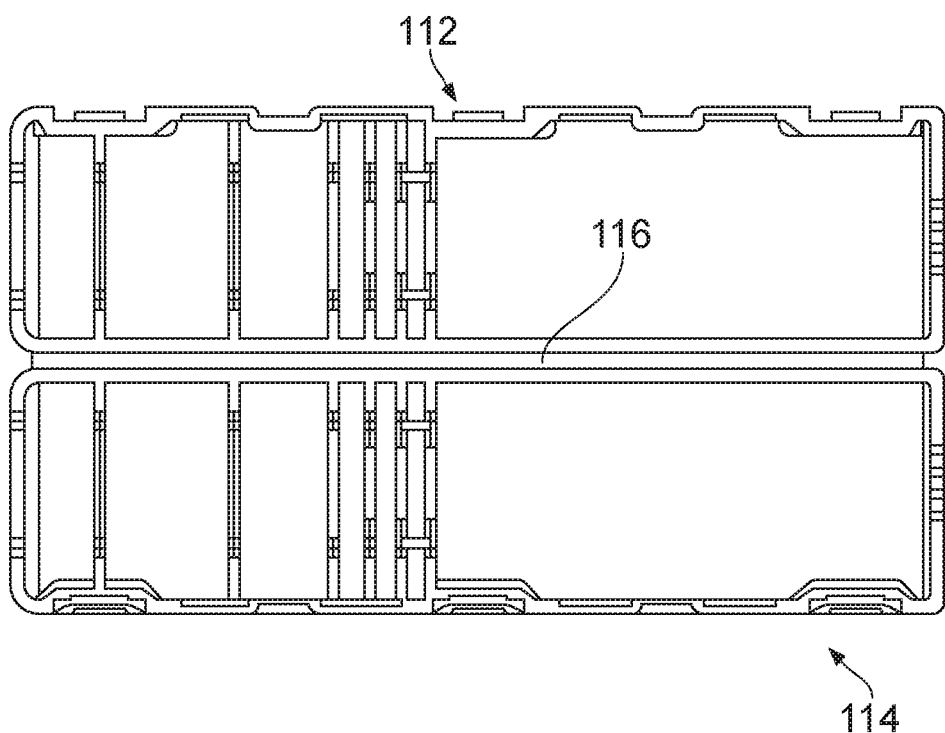
FIG. 4 is a plan view of the opaque housing of the masking package of FIG. 1, in an open configuration.
Figure 5:
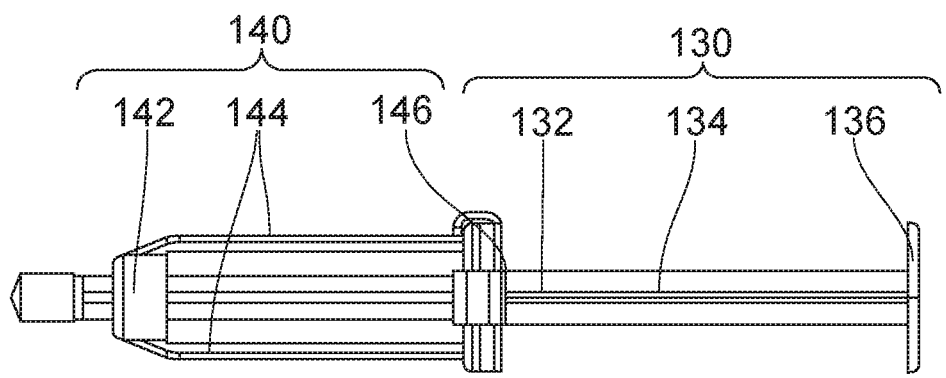
FIG. 5 is a side-on view of the plunger extender and carriage of the masking package of FIG. 5 interacting with a plunger of a syringe.
Figure 6:
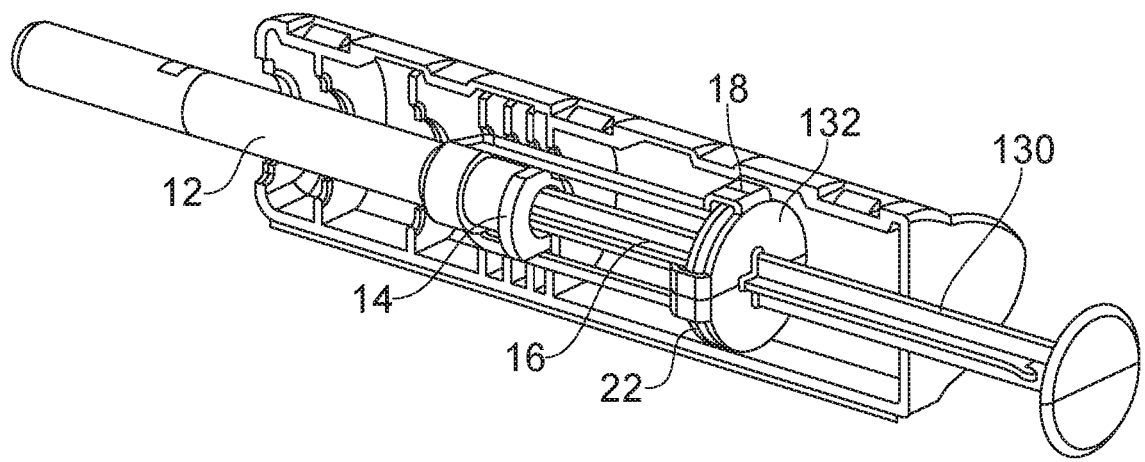
FIG. 6 is a perspective cross-sectional view of the masking package of FIG. 1, without the first housing part.

Referring to FIGS. 1 to 6, the masking package 100 generally comprises an opaque housing 110, a plunger extender 130 and a carriage 140. The carriage 140 is shown in FIGS. 5 and 6. The masking package further includes a second opaque housing 150 substantially surrounding the hypodermic needle (not shown) of the syringe 10 and the needle cover (not shown) disposed over the needle.

Figure 2:
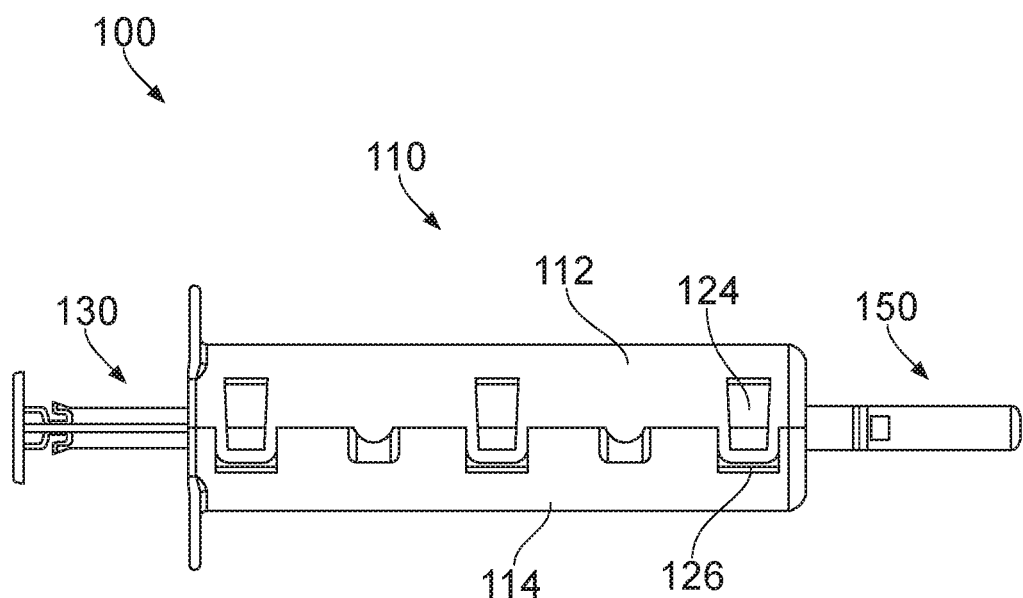
FIG. 2 is a side-on view of the masking package of FIG. 1.

The opaque housing 110 is substantially cylindrical and defines a syringe chamber 111 for receiving the plunger 16 and a major portion of the length of the barrel 12 of the syringe 10. The opaque housing 110 comprises a first housing part 112, a second housing part 114 and a hinge 116 rotatably connecting the first and second housing parts 112, 114. The first and second housing parts 112, 114 are substantially similar in shape and size, being substantially elongate arcs, forming two halves of a hollow cylinder. The opaque housing 110 is formed from a polymeric material by injection moulding. The entire housing 110 is moulded in a single moulding. The hinge 116 is formed by providing a region of reduced thickness compared to the thickness of the first and second housing parts 112, 114 between the first and second housing parts 112, 114. The first and second housing parts 112, 114 are rotatable about the hinge 116 between an open position and a closed position. The open position is shown in FIGS. 3 and 4, which enables the syringe 10 to be laterally inserted into the syringe chamber 111 and laterally removed from the chamber 111. The closed position is shown in FIGS. 1 and 2, which enables the masking package to substantially surround and mask or hide the plunger 16 and a major portion of the barrel of the syringe 10.

The opaque housing 110 comprises a proximal aperture 118 at a proximal end of the housing and a distal aperture 120 at a distal end of the housing, opposite the proximal aperture 118. A proximal portion of the barrel of the syringe extends through the proximal aperture 118 when the syringe is received in the syringe chamber 111.

Each of the first and second housing parts 112, 114 comprises a plurality of complimentary projections 122 extending radially inwards into the syringe chamber 111, at the same position along the length of the housing parts. The projections 112 are spaced to form gaps for receiving the flange 14 at the distal end of the syringe 10. The projections 112 prevent the syringe barrel 12 from moving relative to the opaque housing 110 when the syringe 10 is received in the syringe chamber 111.

The first housing part 112 further comprises locking elements 124, in the form of hooks, extending from the free edge opposite the hinge 116, and spaced apart along the length of the first housing part. The second housing part 114 further comprises complimentary recesses 126 in the outer surface along the free edge opposite the hinge 116. The locking elements 124 and recesses 126 snap fit together when the first and second housing parts are in the closed position, in order to retain the first and second housing parts in the closed position.

The opaque housing 110 also comprises a flange 128 at the distal end of the housing to provide purchase for a user's fingers, in a similar manner to the flange 14 on the barrel 12 of the syringe 10.

The masking package 100 also comprises a plunger extender 130. The plunger extender 130 comprises a coupler 132 at a proximal end, for coupling to the flange 22 of the plunger 16 of the syringe 10, a shaft 134 extending from the coupler 132 in a distal direction and a flange 136 at a distal end. The coupler 132 comprises hooks configured to closely hold the flange 22 of the plunger 16 of the syringe 10 and a flange at a distal end of the carriage 140, described below. The shaft 134 of the plunger extender 130 extends through the aperture at the distal end of the opaque housing 110 and the flange 136 of the plunger extender 130 is larger than the distal aperture of the housing, such that the plunger extender 130 cannot slide fully into the syringe chamber. The plunger extender 130 is slidable in a proximal and distal direction through the distal aperture in the opaque housing 110.

The masking package 100 further comprises a carriage 140. The carriage 140 provides masking for the proximal end of the plunger 16 of the syringe 10. The carriage 140 comprises a ring 142 at a proximal end. The ring 142 has an inner diameter slightly larger than the diameter of the barrel 12 of the syringe, such that the ring 142 may slide up and down the barrel freely. The ring 142 is arranged to substantially surround the stopper of the plunger 16 of the syringe 10 (in FIG. 5 the ring 142 is shown proximal to the stopper of the plunger 16 for clarity, rather than circumscribing the stopper). In this embodiment, the carriage comprises arms 144 extending from the ring 142 in a distal direction to a flange 146 at the distal end. The flange 146 has a similar size and shape to the flange of the plunger 16 of the syringe 10, and is arranged distally of the flange of the plunger 16 of the syringe 10, with the arms 144 extending over the flange of the plunger 16. The coupler 132 of the plunger extender 130 holds both of the flanges of the plunger of the syringe 10 and the carriage 140 together, such that both the plunger of the syringe 10 and the carriage 140 slide with the plunger extender 130.

The proximal aperture at the proximal end of the opaque housing 110 is sized to allow the ring 142 of the carriage to pass through when the plunger extender is moved to a proximal position. As such, the ring 142 of the carriage provides masking for the stopper of the plunger 16 of the syringe 10, when the stopper is pushed beyond the opaque housing 110 of the masking package 100.

Figure 7:
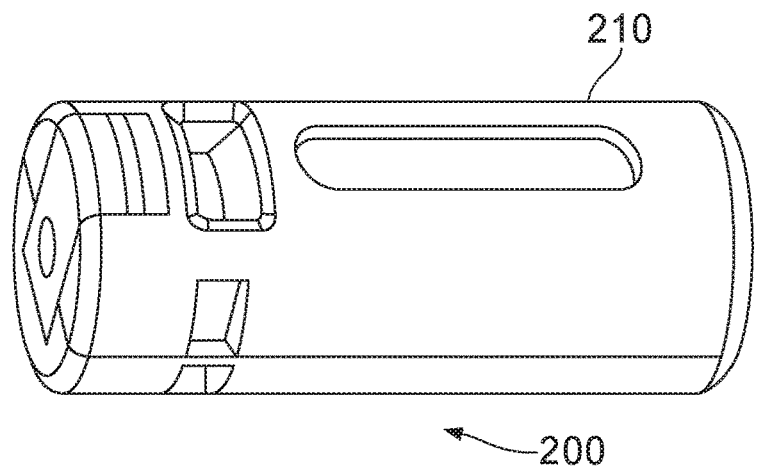
FIG. 7 is a perspective view of a vial mask according to another aspect of the present invention.
Figure 8:
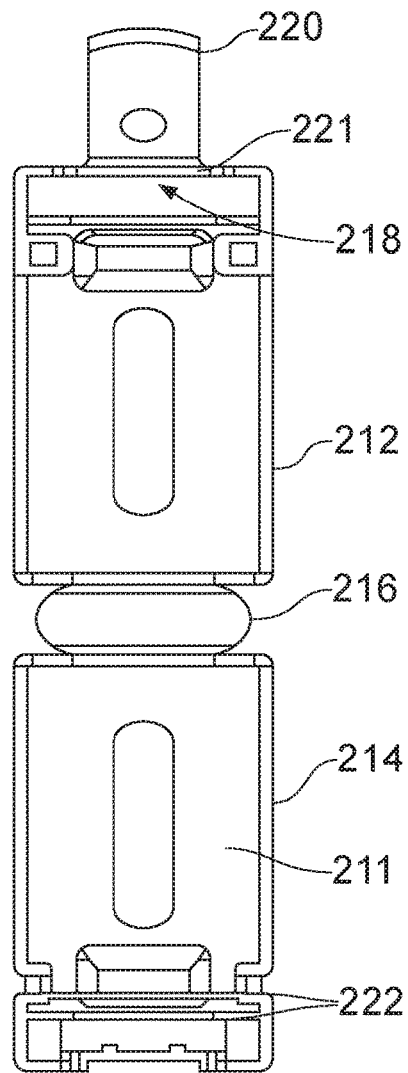
FIG. 8 is a plan view of the vial mask of FIG. 7, in an open configuration.
Figure 9:
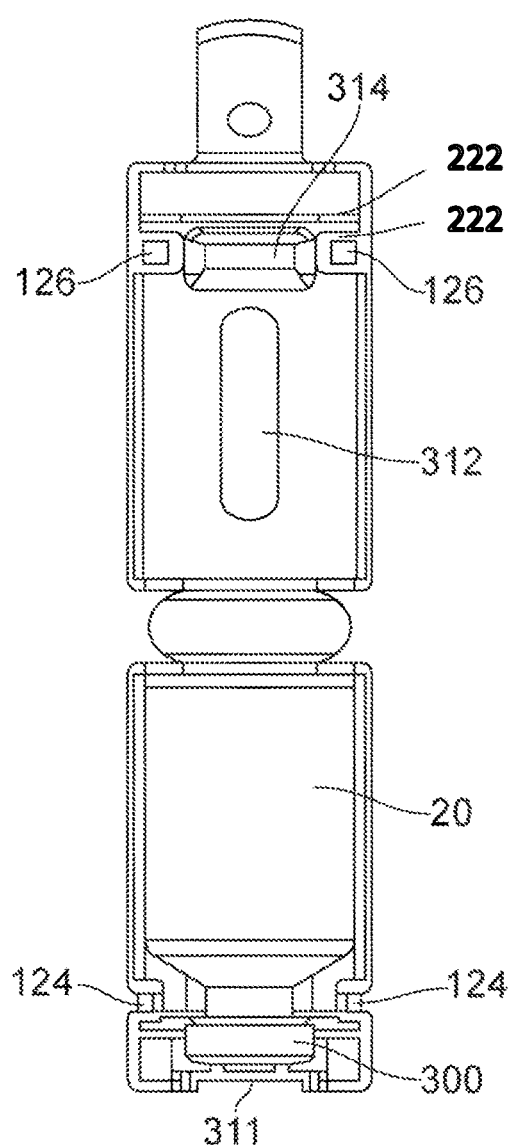
FIG. 9 is a plan view of the vial mask of FIG. 7, in an open configuration, with a vial received in the first housing part of the opaque housing.

Referring to FIGS. 7 to 9, a vial masking package 200 generally comprises an opaque housing 210 for receiving a vial.

The opaque housing 210 is substantially cylindrical and defines a vial chamber 211 for receiving a vial 20. The opaque housing 210 comprises a first housing part 212, a second housing part 214 and a hinge 216 rotatably connecting the first and second housing parts 212, 214. The first and second housing parts 212, 214 are substantially similar in shape and size, being substantially elongate arcs, forming two halves of a hollow cylinder. The opaque housing 210 is formed from a polymeric material by injection moulding. The entire housing 210 is moulded in a single moulding. The hinge 216 is formed by providing a region of reduced thickness compared to the thickness of the first and second housing parts 212, 214 between the first and second housing parts 212, 214. The first and second housing parts 212, 214 are rotatable about the hinge 216 between an open position and a closed position. The open position is shown in FIGS. 8 and 9, which enables the vial 20 to be laterally inserted into the vial chamber 211 and laterally removed from the chamber 211. The closed position is shown in FIG. 7, which enables the vial masking package to substantially surround and mask or hide the vial 20.

The opaque housing 210 comprises an aperture 218 at a first end of the housing. A hinged lid 220 is provided to open and close the aperture. The hinge 221 of that hinged lid 220 is produced by having a region of reduced thickness in a manner similar to that for the hinge 216 discussed above. The aperture is to allow access to the top 311 of a vial 20 and thereby allow a needle attached to a syringe to be inserted through the aperture 218 and vial top or lid 311 into a vial held in the vial mask 210 to access the contents of the vial 20.

The first and second housing parts 112, 114 comprises two pairs of complimentary projections 222, 222 extending radially inwards into the vial chamber 211, at the same position along the length of the housing parts. The projections 222, 222 are spaced to form gaps for receiving the and supporting the upper portion 300 of a vial 20 in the housing. The pair of projections 222 closer to the aperture 218 is sized to surround the engage the sides of the top of the vial; the pair of projections 222 further from the aperture 218 are sized and located to engage the underside of the top of the vial and thereby hold in in place in the vial masking package 210.

The first housing part 212 further comprises locking elements 124, in the form of hooks, extending from the free edge opposite the hinge 216. The second housing part 214 further comprises complimentary recesses 126 in the outer surface along the free edge opposite the hinge 116. The locking elements 124 and recesses 126 snap fit together when the first and second housing parts are in the closed position, in order to retain the first and second housing parts in the closed position.

The vial mask 20 includes a first window 312 located along the longitudinal axis of the vial mask 210, and second a window 314 at the portion of the vial mask 212 adjacent the top 311 of a vial 20 held in the mask 212. The windows 312, 314 are to allow a user to view the contents of vial 20 held in the vial mark 212. The first window 312 allows one to view the main portion of the vial 20 to check, for example, that it is clear and the second window 314 allows one to check the top portion of the vial including checking that the vial 20 is full.

Figure 10:
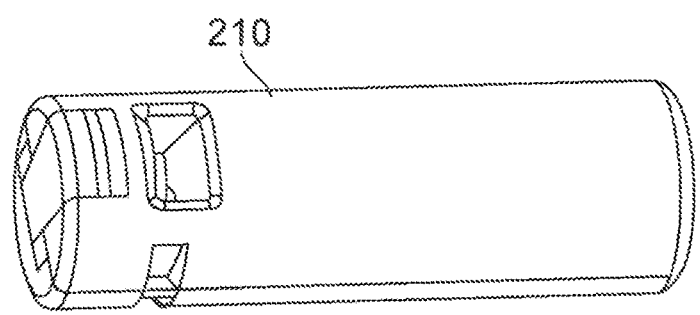
FIG. 10 is a perspective view of a vial mask according to another aspect of the present invention.
Figure 11:
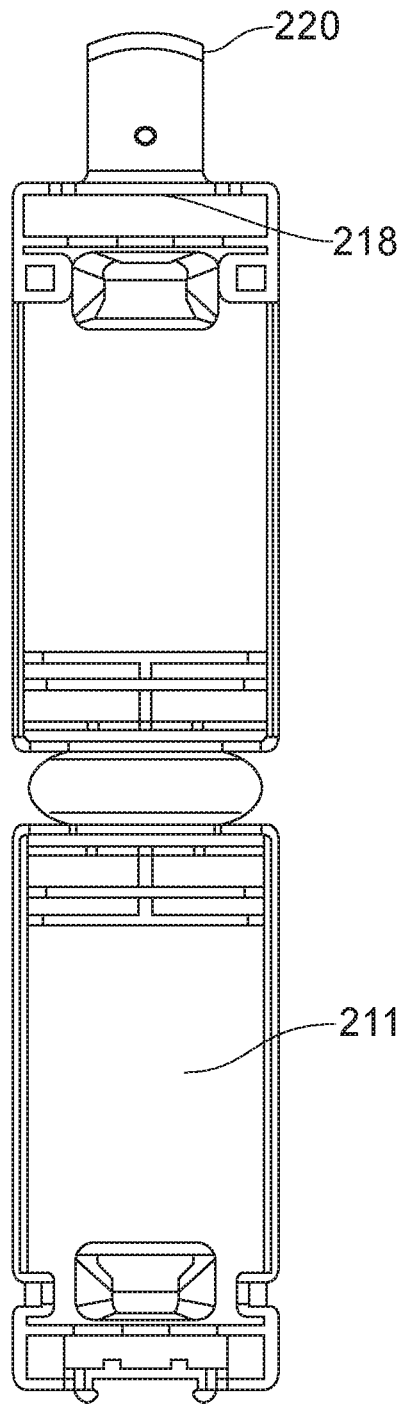
FIG. 11 is a plan view of the vial mask of FIG. 10, in an open configuration.
Figure 12:
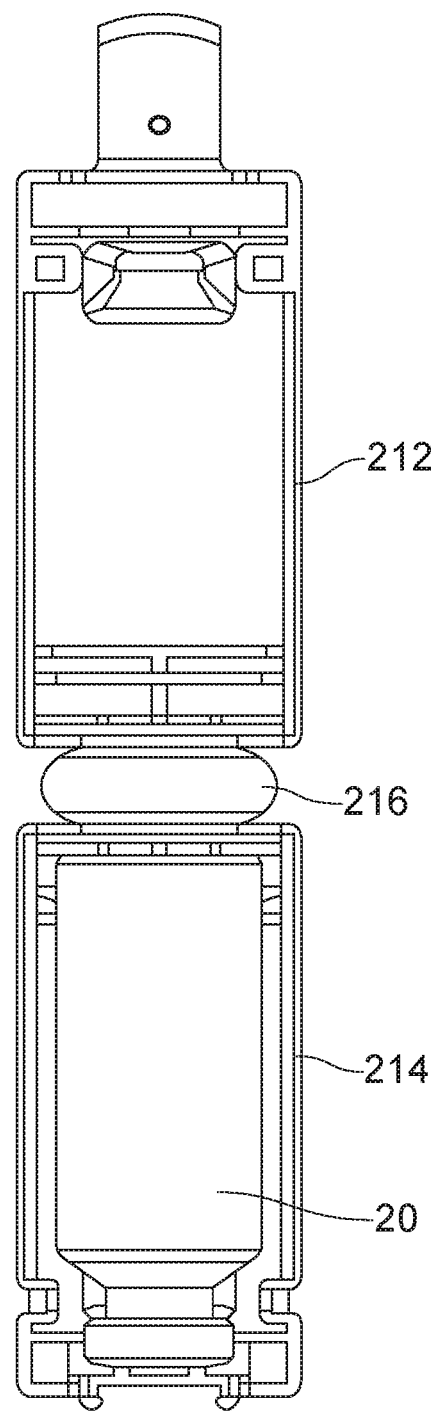
FIG. 12 is a plan view of the vial mask of FIG. 10, in an open configuration, with a vial received in the first housing part of the opaque housing.

FIGS. 10 to 12 illustrate an alternative vial mask 212' which is identical to the vial mask 212 described above with reference to FIGS. 7 to 9 except that it does not include the first window 312.

The invention claimed is:

1. A masking package for blind testing of materials stored in a syringe, the masking package comprising:
   an opaque housing defining a syringe chamber adapted to substantially surround a plunger and at least a portion of a barrel of a syringe; and
   a plunger extender slidably receivable in the syringe chamber and comprising a coupler adapted to couple to the plunger of a syringe received in the syringe chamber, wherein movement of the plunger extender relative to the opaque housing moves the plunger of a syringe received in the syringe chamber relative to the barrel of the syringe.

2. The masking package according to claim 1, wherein the coupler of the plunger extender is adapted to couple to a flange at the distal end of a plunger of a syringe received in the syringe chamber of the housing.

3. The masking package according to claim 1, wherein the masking package further comprises a carriage, the carriage comprising:
   a proximal end slidably receivable over the barrel of a syringe received in the syringe chamber; and
   a distal end adapted to interact with at least one of the plunger extender and the plunger of the syringe when the syringe is received in the syringe chamber of the opaque housing, such that the carriage is movable relative to the barrel of the syringe by movement of the plunger extender into a proximal position relative to the opaque housing.

4. The masking package according to claim 3, wherein the distal end of the carriage is couplable to at least one of the plunger extender and the plunger of a syringe when the syringe is received in the syringe chamber.

5. The masking package according to claim 3, wherein:
   a proximal end of the opaque housing comprises a proximal aperture; and
   the carriage and the proximal aperture are adapted such that at least a proximal end of the carriage is movable through the proximal aperture on movement of the plunger extender into a proximal position relative to the opaque housing.

6. The masking package according to claim 5, wherein:
   the proximal end of the carriage comprises a proximal locking element; and
   the proximal locking element of the carriage and the proximal aperture are adapted to engage with a snap-fit when the plunger extender is in the proximal position.

7. The masking package according to claim 1, wherein:
   the plunger extender comprises a shaft extending between a distal end of the plunger extender and the coupler at the proximal end of the plunger extender; and
   a distal end of the opaque housing comprises a distal aperture, the distal aperture being adapted such that the shaft of the plunger extender extends through the distal aperture when the plunger extender is in the distal position relative to the opaque housing.

8. The masking package according to claim 7, wherein:
   the shaft of the plunger extender comprises a distal locking element towards the distal end of the shaft; and
   the distal aperture and the distal locking element are adapted to engage with a snap-fit when the shaft of the plunger extender is in a proximal position relative to the opaque housing.

9. The masking package according to claim 1, wherein:
   the opaque housing comprises at least one projection extending radially inwards from an inner surface of the syringe chamber, the at least one projection being adapted to engage with a flange at the distal end of a barrel of a syringe received in the syringe chamber to inhibit movement of the barrel in the chamber towards the proximal end of the housing.

10. The masking package according to claim 9, wherein:
    the housing has a length between the proximal end and the distal end; and
    the at least one projection is a plurality of projections comprising at least a pair of projections, the pair of projections extending radially inwards from an inner surface of the syringe chamber and the pair of projections being spaced apart along the length of the housing to form a gap for receiving a flange at the distal end of a barrel of a syringe received in the syringe chamber to inhibit movement of the barrel in the direction of the length of the housing.

11. The masking package according to claim 1, wherein the opaque housing has a length between the proximal end and the distal end and the opaque housing comprises a first part and a second part, the first and second parts being openable along the length of the opaque housing to define an opening in the syringe chamber that extends the length of the housing for inserting a syringe laterally into the syringe chamber.

12. The masking package according to claim 11, wherein the first and second housing parts are rotatably couplable to each other and rotatable between an open position, in which a syringe is insertable into the syringe chamber, and a closed position, in which at least a portion of a syringe received in the syringe chamber is surrounded by the opaque housing.

13. The masking package according to claim 11, wherein at least one of the first and second housing parts comprises a housing locking element for securing the first and second housing parts together in a closed position.

14. The masking package according to claim 1, wherein the opaque housing is a first opaque housing and the masking package further comprises a second opaque housing, the second opaque housing defining a needle chamber for substantially surrounding a needle cover disposed over a needle coupled to a barrel of a syringe received in the syringe chamber of the first opaque housing.

15. The masking package according to claim 14, wherein the second opaque housing comprises a distal opening at a distal end of the second housing for slidably receiving a needle cover and needle in the needle chamber.

16. The masking package according to claim 15, wherein an inner surface of the needle chamber towards the distal opening comprises a locking element adapted to engage with a distal end face of a needle cover disposed over a needle to inhibit the needle cover from being removed from the needle chamber through the distal opening.

17. The masking package according to claim 14, wherein the second housing is separate from the opaque housing.

18. A masking package for blind testing of materials stored in a vial comprising a body and a lid, the masking package comprising:
- an opaque housing defining a vial chamber for receiving and surrounding the body and the lid of the vial, the housing being formed with a single piece construction, the housing comprising:
  - a first housing part comprising opposing upper and lower edges and opposing side edges extending between the upper and lower edges;
  - a second housing part comprising opposing upper and lower edges and opposing side edges extending between the upper and lower edges; and
  - a base portion extending between the lower edges of the first and second housing parts, and rotatably coupled to the lower edges of the first and second housing parts;
- wherein the first and second housing parts are rotatable between an open position, in which the vial is insertable into the vial chamber, and a closed position, in which the vial is surrounded by the opaque housing when the vial is received in the vial chamber;
- wherein the housing has a length between an upper end and a lower end when the housing is in the closed position;
- wherein the first and second housing parts are openable along the length of the housing to define an opening in the vial chamber when the first and second housing parts are in the open position, the opening extending the length of the housing to enable the vial to be inserted laterally into the vial chamber; and
- wherein an aperture is defined at the upper end of the housing between the upper edges of the first and second housing parts when the first and second housing parts are in the closed position, and the lid of the vial is located at or around the aperture when the vial is received in the vial chamber.

19. The masking package according to claim 18, wherein the masking package further comprises a neck support arranged in at least one of the first and second housing parts, the neck support supporting a neck of a vial received in the chamber and inhibiting movement of the vial in the chamber in a direction along the length of the housing.

20. The masking package according to claim 19, wherein the neck support is removably couplable to the opaque housing.

21. The masking package according to claim 19, wherein at least one of the first and second housing parts comprises a locking element for securing the first and second parts together in a closed position.

22. The masking package according to claim 18, wherein the housing further comprises a lid portion rotatably couplable to the upper edge of the second housing part and rotatable between an open position, in which the aperture between the upper edges of the first and second housing parts is uncovered, and a closed position, in which the aperture between the first and second housing parts is covered by the lid portion.

23. The masking package according to claim 18, wherein the opaque housing comprises a window, wherein a portion of a vial received in the vial chamber is visible through the window.

* * * * *